(12) United States Patent
Tinsley

(10) Patent No.: US 12,005,150 B2
(45) Date of Patent: Jun. 11, 2024

(54) APPARATUS FOR CURRENCY STERILIZATION AND EXCHANGE

(71) Applicant: Beverly Tinsley, Fairfield, OH (US)

(72) Inventor: Beverly Tinsley, Fairfield, OH (US)

( * ) Notice: Subject to any disclaimer, the term of this patent is extended or adjusted under 35 U.S.C. 154(b) by 261 days.

(21) Appl. No.: 17/510,567

(22) Filed: Oct. 26, 2021

(65) Prior Publication Data

US 2022/0152250 A1 May 19, 2022

Related U.S. Application Data

(60) Provisional application No. 63/105,443, filed on Oct. 26, 2020.

(51) Int. Cl.
| | | |
|---|---|---|
| *A61L 2/22* | (2006.01) | |
| *A61L 2/26* | (2006.01) | |
| *B65G 15/30* | (2006.01) | |
| *B65G 47/248* | (2006.01) | |
| *B65G 49/00* | (2006.01) | |
| *F26B 15/10* | (2006.01) | |

(52) U.S. Cl.
CPC .................. *A61L 2/22* (2013.01); *A61L 2/26* (2013.01); *B65G 15/30* (2013.01); *B65G 47/248* (2013.01); *B65G 49/00* (2013.01); *F26B 15/10* (2013.01); *A61L 2202/123* (2013.01); *A61L 2202/15* (2013.01)

(58) Field of Classification Search
None
See application file for complete search history.

(56) References Cited

U.S. PATENT DOCUMENTS

| | | | |
|---|---|---|---|
| 7,077,738 B2 * | 7/2006 | Benson | B23Q 11/02 452/149 |
| 11,744,910 B1 * | 9/2023 | Buckner | F26B 5/041 422/28 |
| 2011/0253563 A1 | 10/2011 | Goldman | |

FOREIGN PATENT DOCUMENTS

| | | |
|---|---|---|
| CN | 203894795 U | 10/2014 |
| KR | 20090074939 A | 4/2010 |
| KR | 200478413 Y1 | 10/2015 |
| WO | WO 03/073459 A1 | 9/2003 |

* cited by examiner

*Primary Examiner* — William R Harp
(74) *Attorney, Agent, or Firm* — Jenei LLC

(57) ABSTRACT

An article treating device includes a belt conveyor having a belt that encircles a drive pulley at one end and an idler pulley at another end to support an article. At least one upper sprayer is positioned above the belt and is directed to spray a treatment liquid on an upper surface of the article on the belt. The article treating device sprays a second surface of article using a second sprayer by either: (i) spraying through perforations in a belt of the belt conveyor; and (ii) conveying the article over a flipping wedge to flip over the article before conveying under the second sprayer.

10 Claims, 10 Drawing Sheets

APPARATUS FOR CURRENCY STERILIZATION AND EXCHANGE

CROSS REFERENCE TO RELATED APPLICATION(S)

This patent application claims the benefit of priority under 35 U.S.C. § 119(e) to U.S. Patent Application Provisional Application Ser. No. 63/105,443 entitled "APPARATUS FOR CURRENCY STERILIZATION AND EXCHANGE", filed Oct. 26, 2020, the contents of which are hereby incorporated by reference in their entirety for any purpose.

TECHNICAL FIELD

The present disclosure relates generally to sanitizing machines, and more particularly, to sanitizing machines that automatically spray both sides of flat articles.

BACKGROUND

Many communicable diseases are transferable on contaminated surfaces. Person-to-person interactions often require an exchange of a tangible article, such as a payment means (e.g., paper currency, coins, bank card, bank check, etc.) Handling these articles can provide a vector to transfer contaminants such as viruses, bacteria, etc. from one person's hand to another person's hand. Thus, a payee can require a sanitization of the article prior to accepting the article. However, the payer can also be concerned about losing control of the article prior to completion of the transaction. For example, a dispute could arise if a denomination of currency is placed inside some sanitizing device out of sight of the payer and then the payee asserts that a lower denomination is what was sanitized.

SUMMARY

In one aspect of the present disclosure, an article treating device includes a belt conveyor having a perforated belt that encircles a drive pulley at one end and an idler pulley at another end to support an article. At least one upper sprayer is positioned above the perforated belt and is directed to spray a treatment liquid on an upper surface of the article on the perforated belt. At least one lower sprayer is encircled by the perforated belt and is directed to spray through the perforated belt to an underside of the article.

In another aspect of the present disclosure, an article treating device includes a belt conveyor having a belt that encircles a drive pulley at one end and an idler pulley at another end to support an article. At least one upstream sprayer is positioned above the perforated belt and is directed to spray a treatment liquid on an upper surface of the article on the perforated belt. A flip wedge is positioned to flip over the article conveyed on the belt subsequent to passing the at least one upstream sprayer. At least one downstream sprayer is positioned above the perforated belt and is directed to spray the treatment liquid on an upper surface of the article on the perforated belt subsequent to being flipped by the flip wedge.

In an additional aspect of the present disclosure, a method includes conveying an article from exposed upstream portion of a belt conveyor into a transparent enclosure. The article comprises a tangible payment article placed on the exposed portion by one party to a financial transaction. The method includes conveying the article under a first sprayer that sprays a first surface of the article with a treatment liquid. The method includes spraying a second surface of article using a second sprayer by one of: (i) spraying through perforations in a belt of the belt conveyor; and (ii) conveying the article over a flipping wedge to flip over the article before conveying under the second sprayer.

conveying the article out of the transparent enclosure.

These and other features are explained more fully in the embodiments illustrated below. It should be understood that in general the features of one embodiment also may be used in combination with features of another embodiment and that the embodiments are not intended to limit the scope of the invention.

BRIEF DESCRIPTION OF THE DRAWINGS

The various exemplary embodiments of the present invention, which will become more apparent as the description proceeds, are described in the following detailed description in conjunction with the accompanying drawings, in which.

DETAILED DESCRIPTION

In one or more embodiments, an article treating device includes a belt conveyor having a belt that encircles a drive pulley at one end and an idler pulley at another end to support an article. At least one upper sprayer is positioned above the belt and is directed to spray a treatment liquid on an upper surface of the article on the belt. The article treating device sprays a second surface of article using a second sprayer by either: (i) spraying through perforations in a belt of the belt conveyor; and (ii) conveying the article over a flipping wedge to flip over the article before conveying under the second sprayer.

Figure 1:
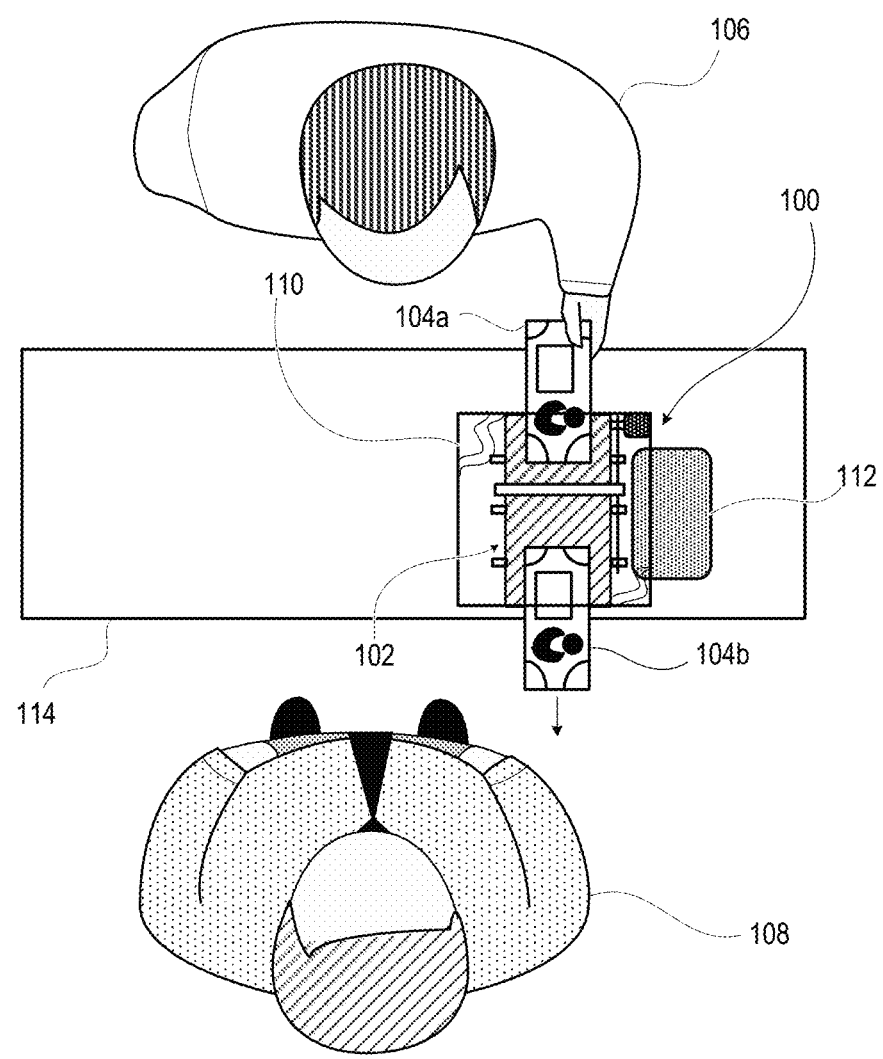
FIG. 1 depicts a top view of an article treatment device having a belt conveyor and treatment liquid spraying that facilitates a transaction between a payer and a payee, according to one or more embodiments.

FIG. 1 depicts a top view of an article treatment device 100 having a belt conveyor 102 that conveys articles, depicted as currency 104a-104b that is being exchanged from a payer 106 to a payee 108. The belt conveyor 102 conveys the currency 104a-104b through a transparent enclosure 110. A treatment liquid spraying system 112 cleans and sanitizes the currency 104a-104b within clear view of both payer 106 and payee 108. The transparent enclosure 110 captures excess treatment liquid to avoid an irritation to payer 106 to a payee 108 as well as enabling economical recirculation. The article treatment device 100 is conveniently sized for placement on a counter 114.

Figure 2A:
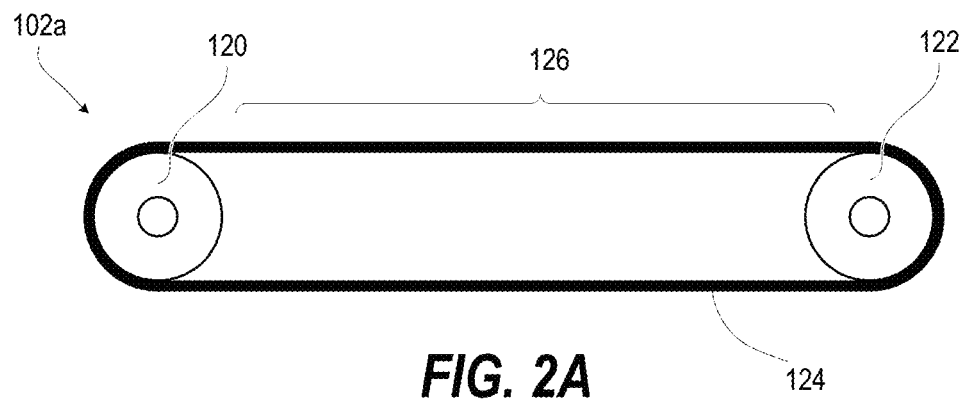
FIG. 2A depicts a side view of pulley-tensioned belt conveyor for the article treatment device of FIG. 1, according to one or more embodiments.

FIG. 2A depicts a side view of a pulley-tensioned belt conveyor 102a for the article treatment device 100 of FIG. 1. A drive pulley 120 and an idler pulley 122 receive a belt 124 that is held in tension to provide a flat conveying surface 126.

Figure 2B:
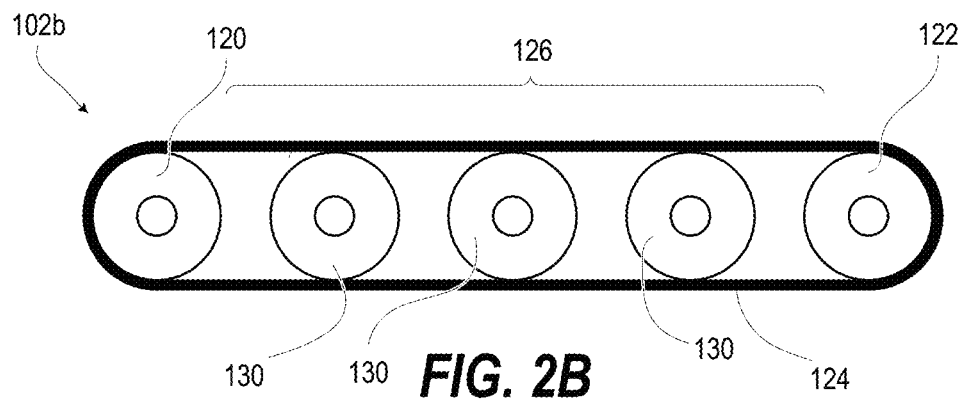
FIG. 2B depicts a side view of a belted roller conveyor for the article treatment device of FIG. 1, according to one or more embodiments.

FIG. 2B depicts a side view of a belted roller conveyor 102b for the article treatment device 100 of FIG. 1. A series of aligned rollers 130 are spaced between the drive pulley 120 and the idler pulley 122 to support the flat conveying surface 126.

Figure 2C:
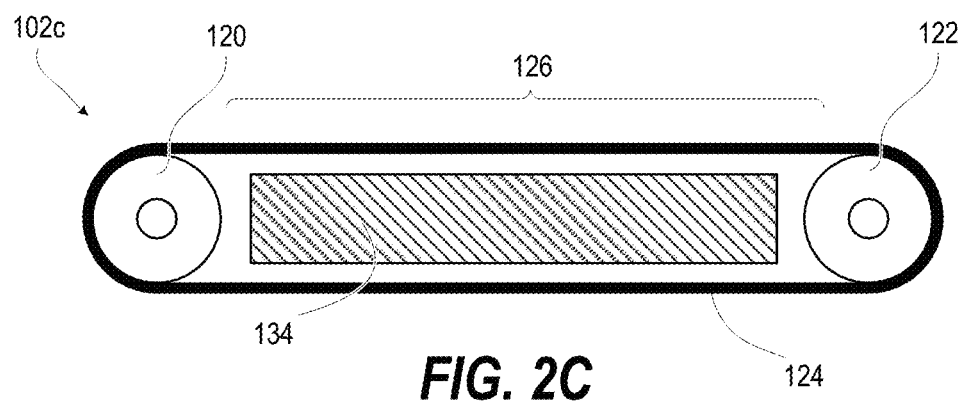
FIG. 2C depicts a side view of a slider tray belt conveyor for the article treatment device of FIG. 1, according to one or more embodiments.

FIG. 2C depicts a side view of a slider tray belt conveyor 102c for the article treatment device 100 of FIG. 1. A slider tray 134 is positioned between the drive pulley 120 and the idler pulley 122 to support the flat conveying surface 126.

Figure 3:
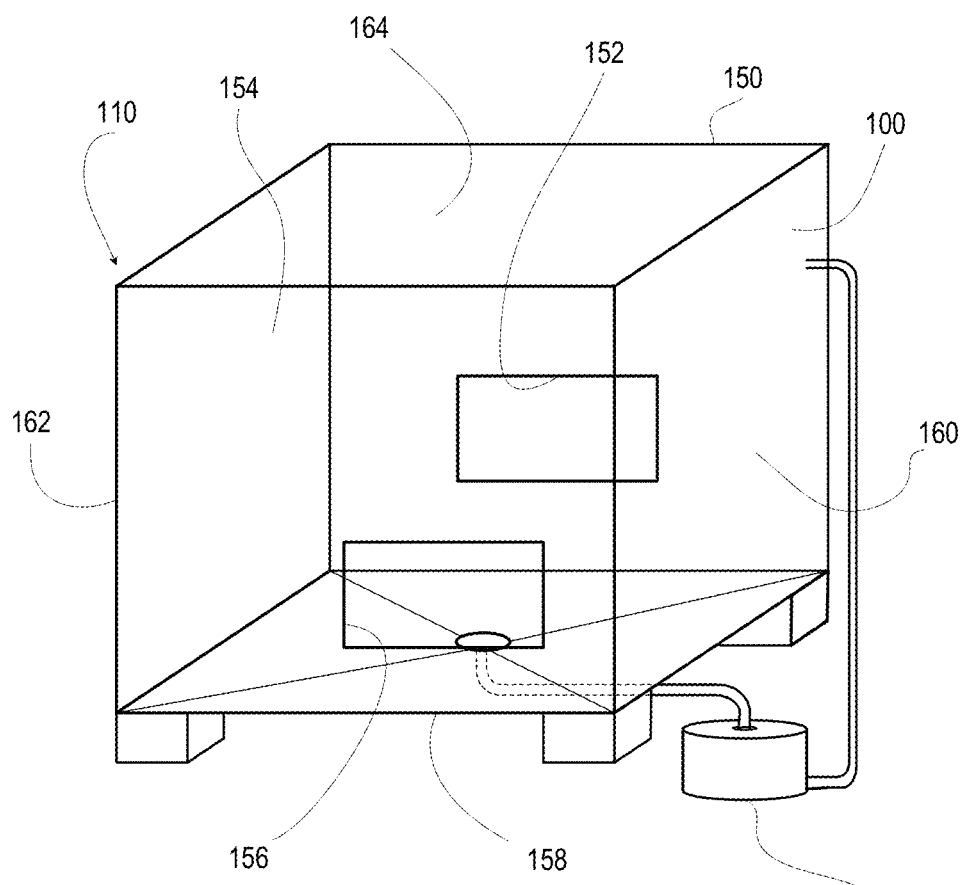
FIG. 3 depicts a three-dimensional view of a transparent enclosure and recirculating treatment liquid system for the article treatment device of FIG. 1, according to one or more embodiments.

FIG. 3 depicts a three-dimensional view of an example transparent enclosure 110 and recirculating treatment liquid spraying system 112 for the article treatment device 100 of FIG. 1. In one or more embodiments, the transparent enclosure 100 is rectangular with an upstream lateral wall 150 having an upstream conveyor opening 152 that is opposed by a downstream lateral wall 154 having a downstream conveyor opening 156. A funnel bottom 158 collects excess treatment liquid for recirculating by treatment liquid spraying system 112. Left, right and top walls 160, 162, 164 complete the enclosure and are transparent to provide viewing from any direction. In one or more embodiments, the transparent enclosure 110 is formed from acrylic sheets.

Figure 4:
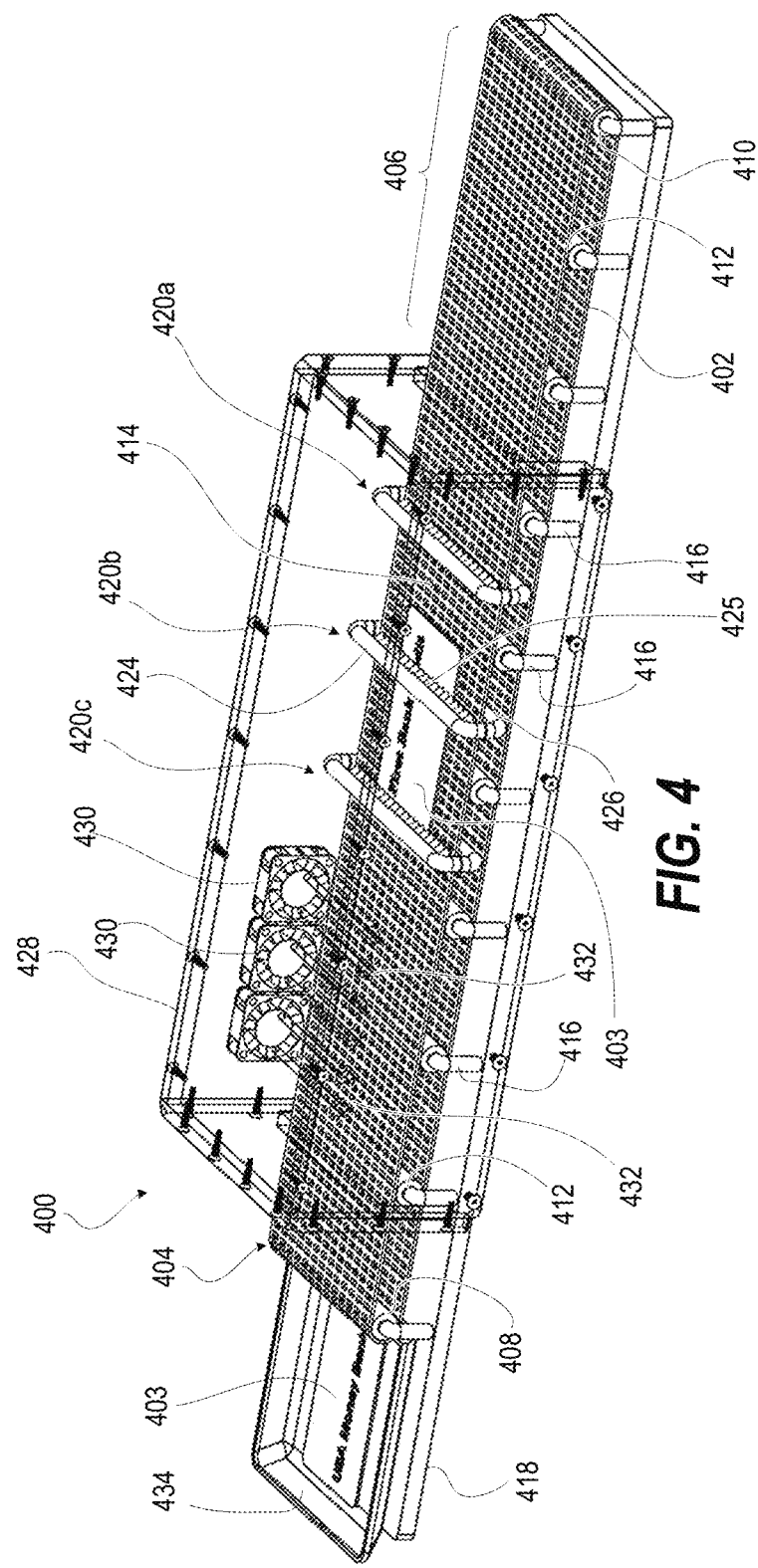
FIG. 4 depicts a three-dimensional view of an example article treatment device having a perforated belt for dual sided treatment, according to one or more embodiments.
Figure 5:
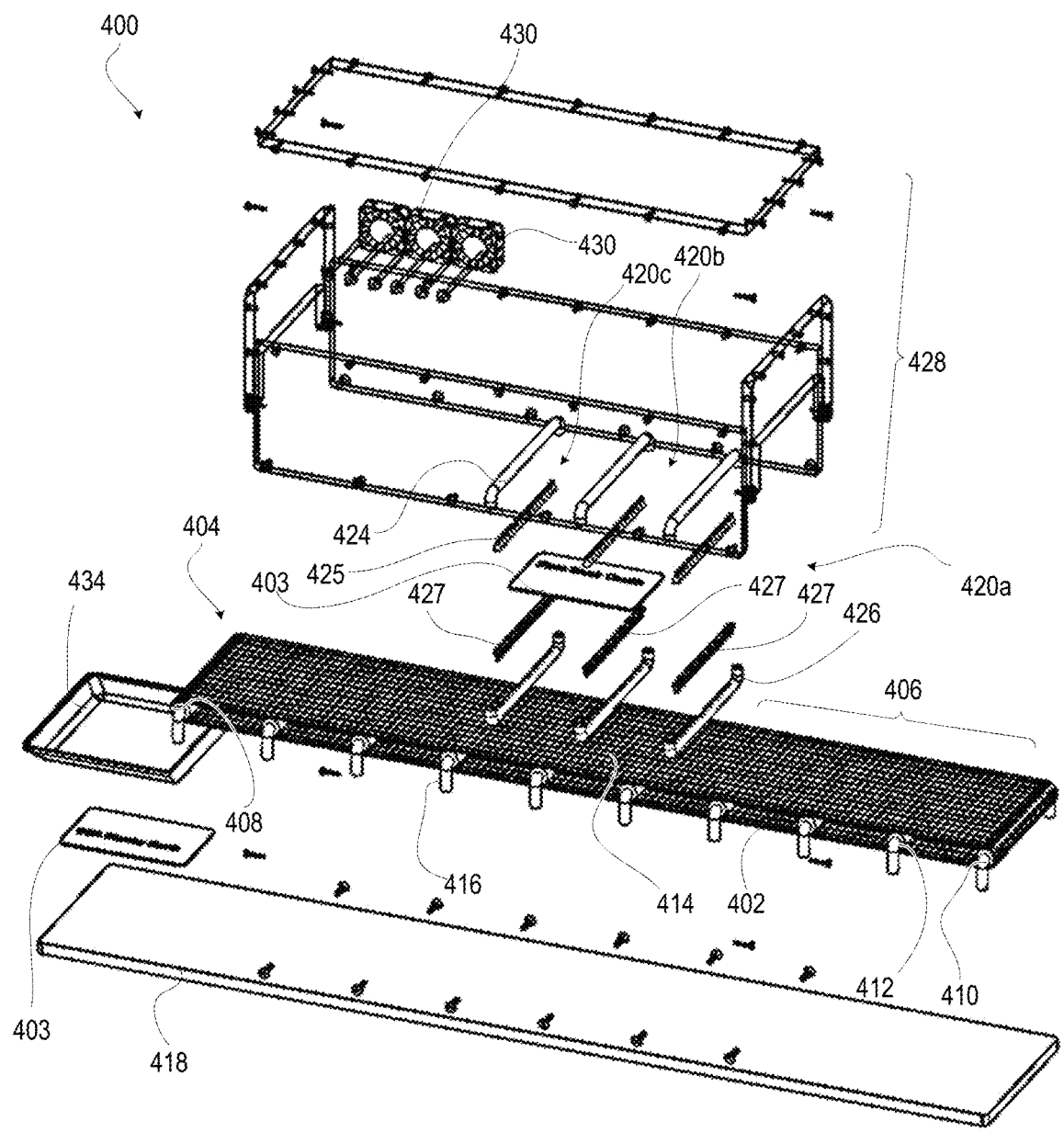
FIG. 5 depicts a three-dimensional exploded view of the example article treatment device of FIG. 4, according to one or more embodiments.
Figure 6:
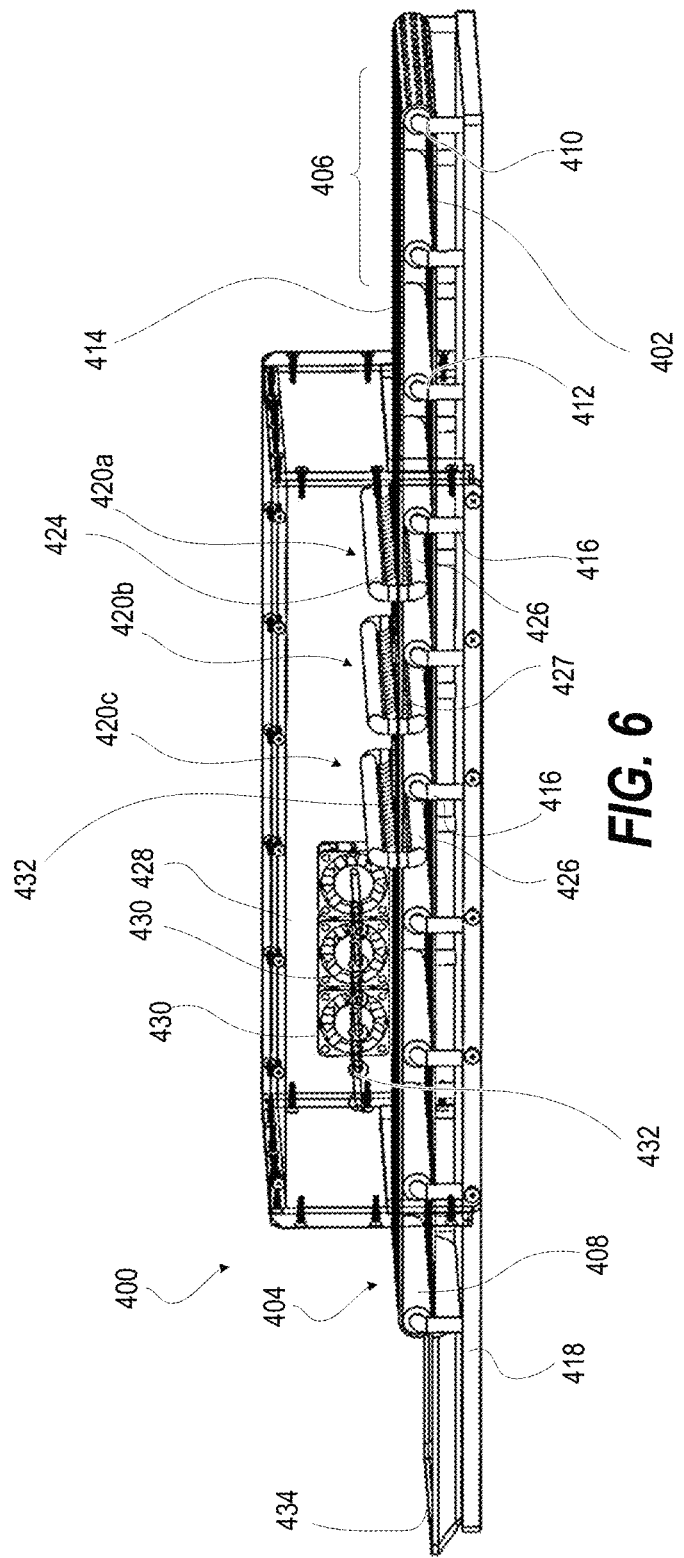
FIG. 6 depicts a side view of the example article treatment device of FIG. 4, according to one or more embodiments.

FIG. 4 depicts a three-dimensional view of an example article treatment device 400 having a perforated belt 402 for dual sided treatment of an article 403. FIG. 5 depicts a three-dimensional exploded view of the example article treatment device 400. FIG. 6 depicts a side view of the example article treatment device 400. With reference to FIGS. 4-6, the article treatment device 400 includes an elongate belted roller conveyor 404 that has an exposed upstream portion 406 that accepts the article 403 to be cleaned and sanitized. The perforated belt 402 encircles drive and idler pulleys 408, 410 on opposite ends with a series of spaced rollers 412 supporting a flat conveying surface 414. Each roller 412 and pulley 408, 410 are attached at opposite ends by support legs 416 to a base 418. Three buckle-shaped sprayers 420a-420c encircle the flat conveying surface 414. Each sprayer 420a-420c has an upper spray bar 424 that has downward nozzles 425 that spray downward toward the perforated belt 402 and a lower spray bar 426 that has upward nozzles 427 that spray upward through the perforated belt 402. A transparent enclosure 428 encloses a substantial portion of the belted roller conveyor 404 including the sprayers 420a-420c. Three fan modules 430 downstream of the sprayers 420a-420c exhaust air through a right side of the transparent enclosure 428, draw-ing air through vent holes 432 on a left side of the transparent enclosure 428 to dry the article 403 after being sprayed. Further downstream, the article 403 is conveyed out of the transparent enclosure 428 and deposited in a tray 434.

Figure 7:
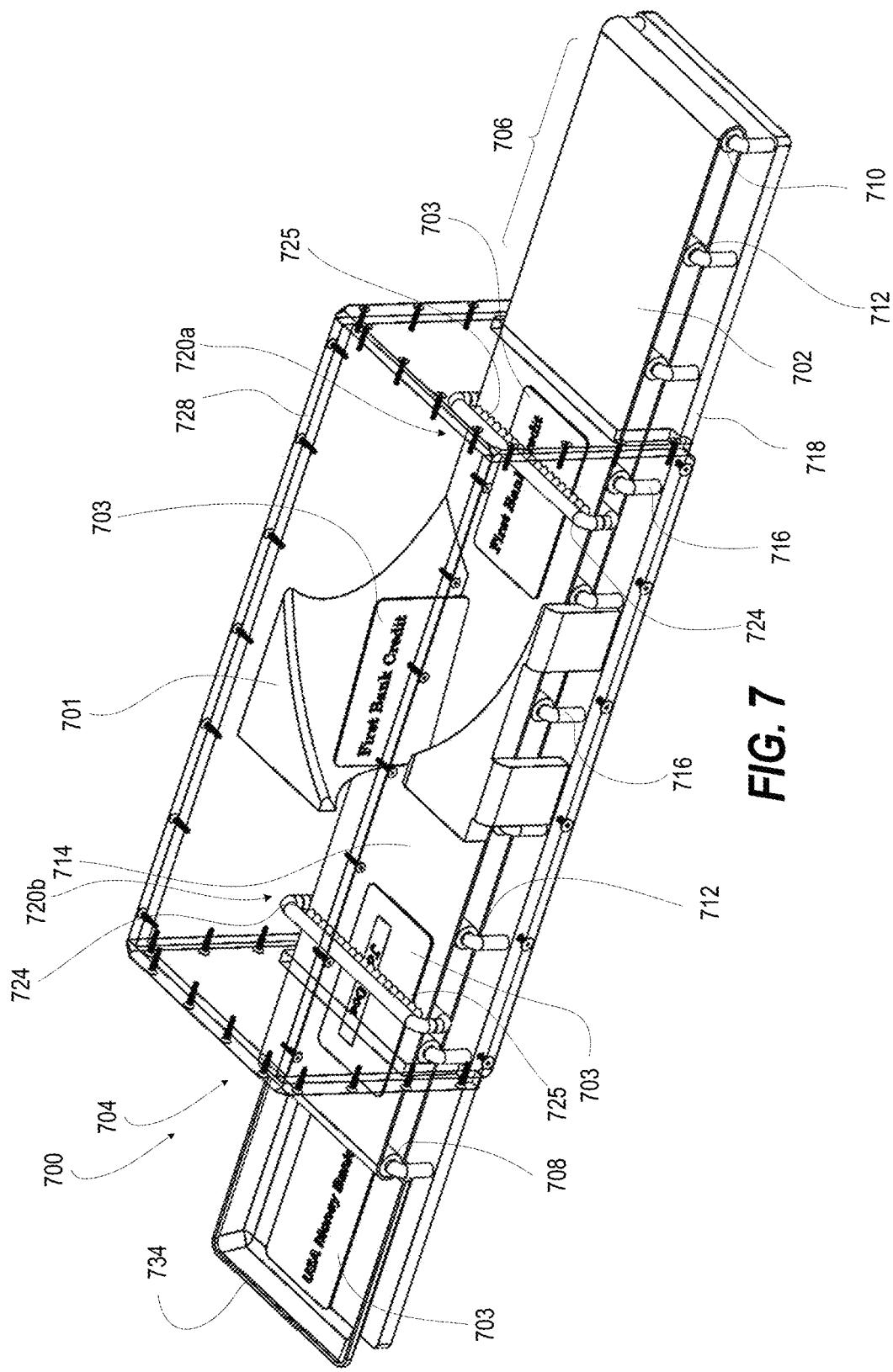
FIG. 7 depicts a three-dimensional view of an example article treatment device having a flip wedge for dual sided treatment, according to one or more embodiments.
Figure 8:
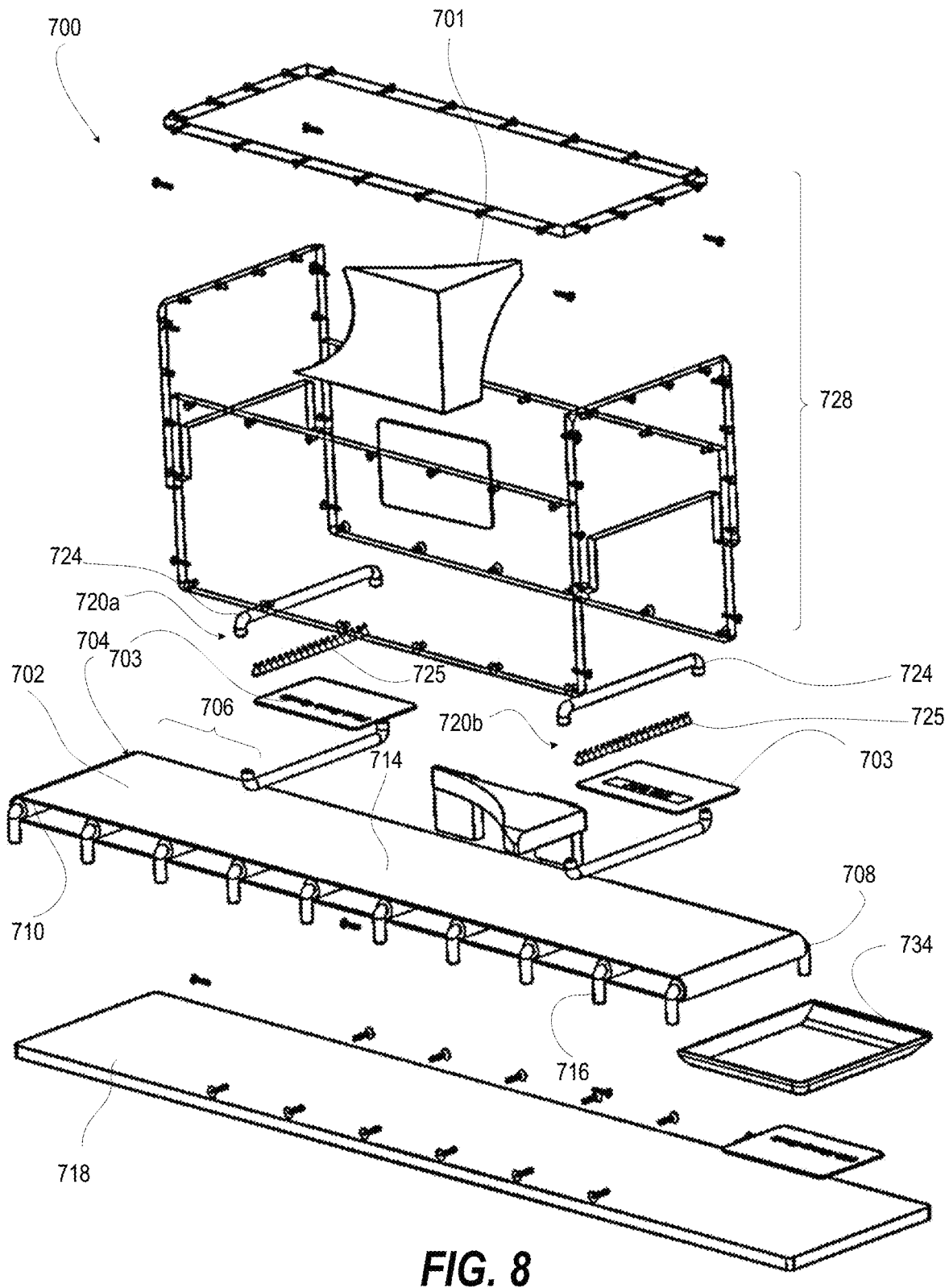
FIG. 8 depicts a three-dimensional exploded view of the example article treatment device of FIG. 7, according to one or more embodiments.
Figure 9:
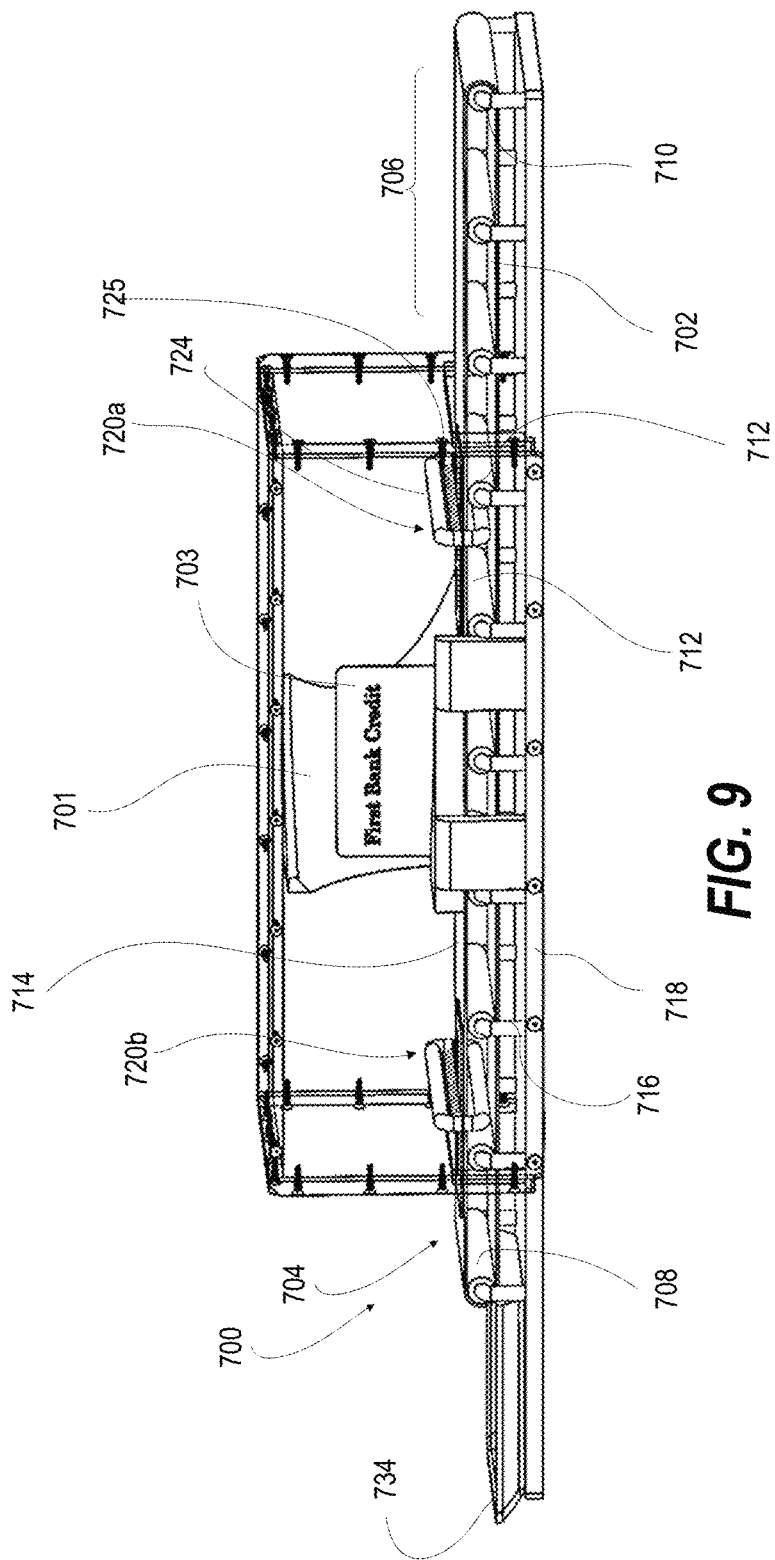
FIG. 9 depicts a side view of the example article treatment device of FIG. 7, according to one or more embodiments.

FIG. 7 depicts a three-dimensional view of an example article treatment device 700 having a flip wedge 701 above a belt 702 for dual sided treatment of an article 703. FIG. 8 depicts a three-dimensional exploded view of the example article treatment device 700. FIG. 9 depicts a side view of the example article treatment device 700. With reference to FIGS. 7-9, the article treatment device 700 includes an elongate belted roller conveyor 704 that has an exposed upstream portion 706 that accepts the article 703 to be cleaned and sanitized. The belt 702 encircles drive and idler pulleys 708, 710 on opposite ends with a series of spaced rollers 712 supporting a flat conveying surface 714. Each roller 712 and pulley 708, 710 are attached at opposite ends by support legs 716 to a base 718. Upstream and downstream buckle-shaped sprayers 720a-720b encircle the flat conveying surface 714. Each sprayer 720a-720b has an upper spray bar 724 that has downward nozzles 425 that spray downward toward the belt 702. The flip wedge 701 is positioned between upstream and downstream buckle-shaped sprayers 720a-720b. The flip wedge 701 turns over the article 703. A transparent enclosure 728 encloses a substantial portion of the belted roller conveyor 704 including the sprayers 724, 726. Further downstream, the article 703 is conveyed out of the transparent enclosure 728 and deposited in a tray 734.

Figure 10:
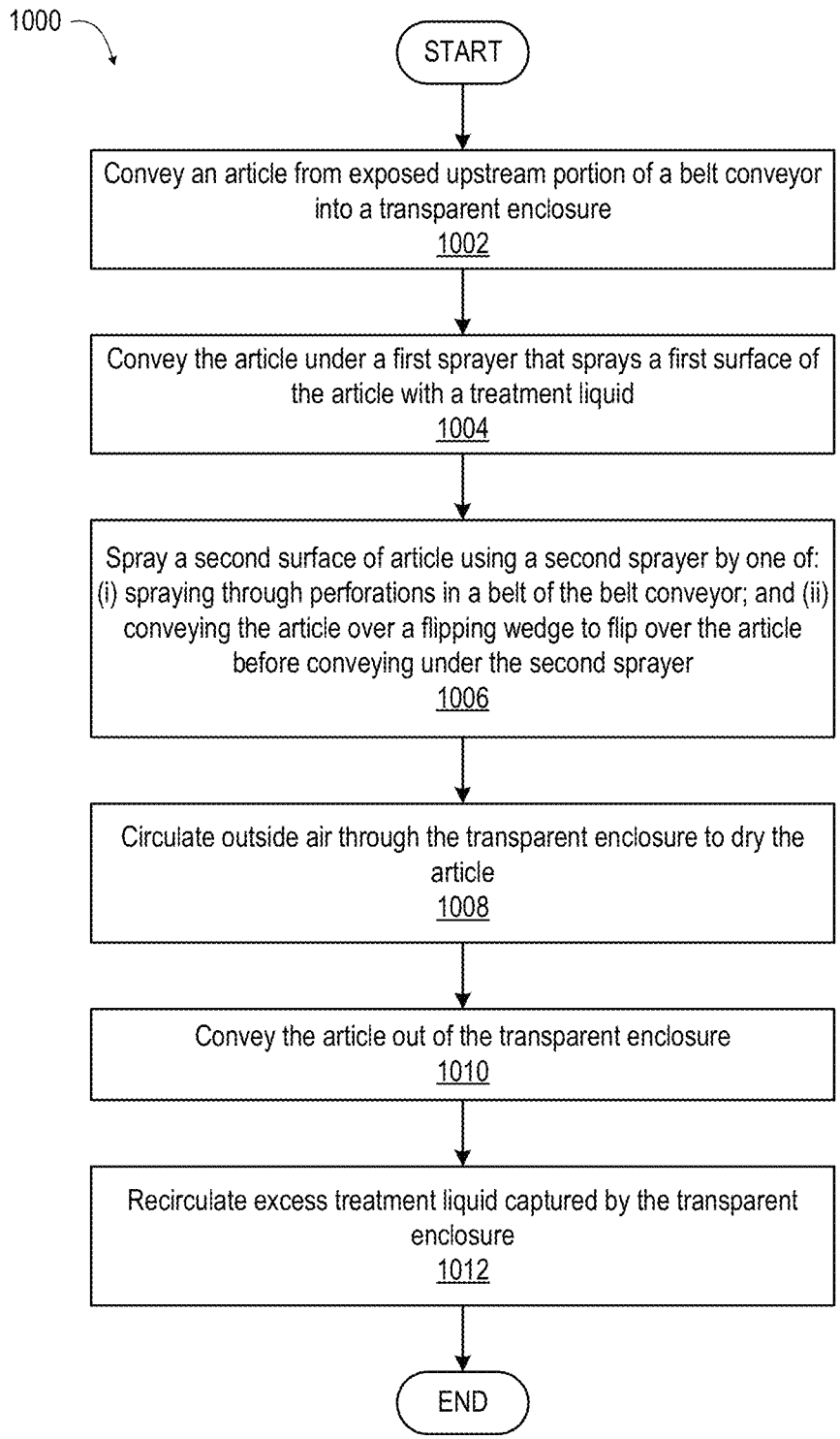
FIG. 10 presents a flow diagram of a method for facilitating a transaction between a payer and a payee by automated treatment liquid spraying of a payment article, according to one or more embodiments.

FIG. 10 presents a flow diagram of a method 1000 for facilitating a transaction between a payer and a payee by automated treatment liquid spraying of a payment article. The method 1000 includes conveying an article from exposed upstream portion of a belt conveyor into a transparent enclosure (block 1002). The article is a tangible payment article (e.g., currency, coin, bank card, check, etc.) placed on the exposed portion by one party to a financial transaction. The method 1000 includes conveying the article under a first sprayer that sprays a first surface of the article with a treatment liquid (block 1004). The method 1000 includes spraying a second surface of article using a second sprayer by one of: (i) spraying through perforations in a belt of the belt conveyor; and (ii) conveying the article over a flipping wedge to flip over the article before conveying under the second sprayer (block 1006). The method 1000 includes circulating outside air through the transparent enclosure to dry the article (block 1008). The method 1000 includes conveying the article out of the transparent enclosure (block 1010). The method 1000 includes recirculating excess treatment liquid captured by the transparent enclosure (block 1012). Then method 1000 ends.

In one or more embodiments illustrated in FIGS. 1-10, the article treatment device 100 comprises a hand sterilization module (not shown). The hand sterilization module allows a user to sterilize their hands after purchase and prior to retrieving the purchased product. The hand sterilization module comprises a sterilizing material compartment, a dispenser, a sensor, and a hand sterilizing area. The sterilizing material compartment stores a germicidal or sterilizing gel or sterilizing liquid. The dispenser is connected to the sterilizing material compartment and sprays the sterilizing liquid or pumps out the sterilizing gel from the sterilizing material compartment. A least one sensor is provided to sense when a user inserts their hands into the hand sterilizing area and signals the dispenser to dispense the sterilizing gel or liquid onto the user's hands in the hand sterilizing area.

The user simply rubs their hands and the sterilizing material sterilizes the user's hands. In application, the user selects the product they want to purchase and inserts payment into the payment area of the article treatment device 100. The payment controller signals the hands sterilizing module that a purchase has been made. The user inserts their hands into the hand sterilizing area and the dispenser dispenses the sterilizing material to sterilize the user's hands. The user, having sterilized hands, can now retrieve their purchased sanitary product from the sanitary dispensing machine.

In one or more embodiments illustrated in FIGS. 1-10, the article treatment device 100 comprises ultraviolet light sterilization module according to an embodiment of the present invention. In one or more embodiments, the article treatment device 100 further comprises an ultraviolet light module positioned inside or around the coin currency input. In this embodiment the ultraviolet light module is provided for performing sterilization procedures on the coins input by a user into the coin currency input. The ultraviolet light module comprises a lamp or a plurality of lamps, for example, a mercury-vapor lamp that emits ultraviolet light at the germicidal wavelength. Since money is frequency passed between people, stored in unhygienic areas, touched by hands or devices, money such as coin currency or paper currency is carries and passes germs or bacteria and is usually unsanitary. The ultraviolet light module sterilizes the coins by breaking down micro-organisms. Ultraviolet light has a short wavelength that is harmful to microorganisms and destroys their nucleic acids. The ultraviolet radiation disrupts the microorganisms' DNA thereby killing them by eliminating their reproductive capabilities. Microorganisms cannot survive prolonged exposure to ultraviolet light.

It will be apparent to those skilled in the art that various modifications and variations can be made to the disclosed system. Other examples will be apparent to those skilled in the art from consideration of the specification and practice of the disclosed system. By way of non-limiting examples, magnets, buckles, buttons, or other attaching mechanisms could be used in the place of fastener surfaces. It is intended that the specification and examples be considered as illustrative only, with a true scope being indicated by the following claims and their equivalents.

What is claimed is:

1. An article treating device comprising:
   a belt conveyor having a perforated belt that encircles a drive pulley at one end and an idler pulley at another end to support an article;
   at least one upstream sprayer positioned above the perforated belt and directed to spray a treatment liquid on an upper surface of the article on the perforated belt;
   a flip wedge positioned to flip over the article conveyed on the perforated belt subsequent to passing the at least one upstream sprayer; and
   at least one downstream sprayer positioned above the perforated belt and directed to spray the treatment liquid on an upper surface of the article on the perforated belt subsequent to being flipped by the flip wedge.

2. The article treating device of claim 1, wherein the belt conveyor comprises a roller conveyor having an aligned series of live rollers spaced between the drive pulley and the idler pulley that are supported for rotation by a base.

3. The article treating device of claim 1, wherein the belt conveyor comprises a slider bed positioned between the drive pulley and the idler pulley.

4. The article treating device of claim 1, wherein drive pulley and the idler pulley are supported in opposition to apply tension that flattens the perforated belt.

5. The article treating device of claim 1, wherein the perforated belt has a lateral width having a size sufficiently wide to convey the article that comprises a tangible payment article of one or more of: (i) coins; (ii) currency; (iii) credit cards and sufficiently small to be supported upon a counter.

6. The article treating device of claim 1, further comprising an enclosure received over a portion of the belt conveyor to capture excess treatment liquid and to enable two parties to view the article during a transaction of: (i) placement on the perforated belt by one party; (ii) transporting of the article through the transparent enclosure; and (iii) depositing the article off of an end of the belt conveyor.

7. The article treating device of claim 6, further comprising a funnel bottom configured to collect excess treatment liquid for recirculation.

8. The article treating device of claim 6, further comprising one or more fan modules positioned to move air through the enclosure to facilitate drying of treated articles.

9. A method comprising:
   conveying an article from exposed upstream portion of a belt conveyor into a enclosure, the article comprising a tangible payment article placed on the exposed portion by one party to a financial transaction;
   conveying the article under at least one first sprayer positioned upstream that sprays a first surface of the article with a treatment liquid;
   spraying a second surface of the article using at least one second sprayer positioned downstream by conveying the article over a flipping wedge to flip over the article before conveying under the at least one second sprayer; and
   conveying the article out of the enclosure.

10. The method of claim 9, further comprising:
    recirculating excess treatment liquid captured by the enclosure; and
    circulating outside air through the enclosure to dry the article.

* * * * *